(12) United States Patent
Sung et al.

(10) Patent No.: US 6,624,138 B1
(45) Date of Patent: Sep. 23, 2003

(54) DRUG-LOADED BIOLOGICAL MATERIAL CHEMICALLY TREATED WITH GENIPIN

(75) Inventors: Hsing-Wen Sung, Hsinchu (TW); Hosheng Tu, Newport Beach, CA (US)

(73) Assignee: GP Medical, Newport Beach, CA (US)

( * ) Notice: Subject to any disclaimer, the term of this patent is extended or adjusted under 35 U.S.C. 154(b) by 0 days.

(21) Appl. No.: 10/211,656

(22) Filed: Aug. 2, 2002

Related U.S. Application Data

(63) Continuation-in-part of application No. 09/297,808, filed as application No. PCT/US97/20113 on Nov. 4, 1997.
(60) Provisional application No. 60/030,701, filed on Nov. 5, 1996, and provisional application No. 60/393,565, filed on Jul. 2, 2002.

(51) Int. Cl.$^7$ .............................................. A61K 31/00
(52) U.S. Cl. ............................... 514/1; 514/4; 514/356; 530/356; 549/396; 424/422; 424/423
(58) Field of Search ................... 424/422, 423; 514/1, 4, 456; 530/356; 549/396

(56) References Cited

U.S. PATENT DOCUMENTS

| | | | |
|---|---|---|---|
| 4,806,595 A | 2/1989 | Noshiki et al. | |
| 5,037,664 A | 8/1991 | Kyogoku et al. | |
| 5,270,446 A | 12/1993 | Kyogoku et al. | |
| 5,322,935 A | 6/1994 | Smith | |
| 5,516,781 A | 5/1996 | Morris et al. | |
| 5,886,026 A | 3/1999 | Hunter et al. | |
| 5,929,038 A | 7/1999 | Chang | |
| 6,103,255 A | 8/2000 | Levene et al. | |
| 6,162,826 A | 12/2000 | Moon et al. | |
| 6,206,931 B1 | 3/2001 | Cook et al. | |
| 6,262,083 B1 | 7/2001 | Moon et al. | |
| 6,264,992 B1 | 7/2001 | Voytik-Harbin et al. | |
| 6,395,300 B1 | 5/2002 | Straub et al. | |
| 2002/0091445 A1 | 7/2002 | Sung et al. | |

FOREIGN PATENT DOCUMENTS

| | | |
|---|---|---|
| EP | 0366998 | 10/1989 |
| WO | WO 98/19718 | 5/1998 |

OTHER PUBLICATIONS

Hsing–Wen Sung et al., "Fixation of biological tissues with a naturally occurring crosslinking agent: fixation rate and effects of pH, temperature, and initial fixative concentration" J Biomed Mat Res; 2000; 52:077–87.

Chen–Chi Tsai, et al., "In vitro evaluation of the genotoxicity of a naturally occurring crosslinking agent (genipin) for biologic tissue fixation" J Biomed Mater Res, 2000; 52: 58–65.

Hsing–Wen Sung et al., "Mechanical properties of a porcine aortic valve fixed with a naturally occurring crosslinking agent" Biomaterials 1999; 20: 1759–1772.

Hsing–wen Sung et al., "In vitro evaluation of cytotoxicity of a naturally occurring cross–linkng reagent for biological tissue fixation" J Biomater Sci. Polymer Edu, vol. 10, No. 1, pp. 63–78 (1999).

Fwu–Long Li, et al., "In Vivo biocompatibility and degradability of a novel injectable–chitosan–based implant", Biomaterials 23(2002) 181–191.

Yen Chang et al., "Reconstruction of the right ventricular outflow tract with a bovine jugular vein graft fixed with a naturally occurring crosslinking agent (genipin) in a canine model" J Thorac Cardiovasc Surg 2001; 122: 1208–18.

*Primary Examiner*—Samuel Barts
*Assistant Examiner*—Ganapathy Krishnan

(57) ABSTRACT

A method for treating tissue of a patient comprising, in combination, mixing a drug with a solidifiable biological material, chemically treating the drug with the biological material with a crosslinking agent, loading the solidifiable drug-containing biological material onto a medical device, solidifying the drug-containing biological material; and delivering the medical device to a target tissue for treating the tissue.

30 Claims, 7 Drawing Sheets

DRUG-LOADED BIOLOGICAL MATERIAL CHEMICALLY TREATED WITH GENIPIN

CROSS-REFERENCE TO RELATED APPLICATIONS

This patent application is a continuation-in-part application of application Ser. No. 09/297,808 filed Sep. 27, 2001, entitled "Chemical modification of biomedical materials with genipin", which is the national stage entry of PCT/US97/20113 filed Nov. 4, 1997, which claims the benefits of a provisional application Ser. No. 60/030,701 filed Nov. 5, 1996. This patent application also claims the benefits of a provisional application Ser. No. 60/393,565 filed Jul. 2, 2002, entitled "Solidifiable biological material chemically treated with genipin", incorporated herein by reference in its entirety.

FIELD OF THE INVENTION

The present invention generally relates to chemical modification of biomedical materials, such as collagen matrix with a naturally occurring crosslinking reagent, genipin. More particularly, the present invention relates to solidifiable collagen-containing and/or chitosan-containing biological material loaded with drug that is configured suitable for drug slow release effective for therapeutic purposes, wherein the biological material is chemically treated with a crosslinking reagent, genipin, its derivatives or analog and the process of manufacture thereof.

BACKGROUND OF THE INVENTION

Crosslinking of Biological Material

Crosslinking of biological molecules is often desired for optimum effectiveness in biomedical applications. For example, collagen, which constitutes the structural framework of biological tissue, has been extensively used for manufacturing bioprostheses and other implanted structures, such as vascular grafts, wherein it provides a good medium for cell infiltration and proliferation. However, biomaterials derived from collagenous tissue must be chemically modified and subsequently sterilized before they can be implanted in humans. The fixation, or crosslinking, of collagenous tissue increases strength and reduces antigenicity and immunogenicity. In one aspect of the present invention, crosslinking of a drug-containing biological material with genipin enables the resulting material ("biological substance") with less antigenicity or immunogenicity, wherein the biological material comprises collagen, gelatin, elastin, chitosan, NOCC (N, O, Carboxylmethyl Chitosan), and the like that has at least one amino functional group for reaction with genipin.

Collagen sheets are also used as wound dressings, providing the advantages of high permeability to water vapor and rapid wound healing. Disadvantages include low tensile strength and easy degradation of collagen by collagenase. Crosslinking of collagen sheets reduces cleavage by collagenase and improves tensile strength. In one aspect of the present invention, a collagen strip derived of crosslinked drug-containing collagen sheets may be used to load on the periphery of a stent as a drug-eluting stent to mitigate restenosis or other abnormality. In a further aspect of the present invention, the collagen sheet or collagen strip may be made of solidifiable collagen.

Clinically, biological tissue has been used in manufacturing heart valve prostheses, small-diameter vascular grafts, ligament replacements, and biological patches, among others. However, the biological tissue has to be fixed with a crosslinking or chemically modifying agent and subsequently sterilized before they can be implanted in humans. The fixation of biological tissue or collagen is to reduce antigenicity and immunogenicity and prevent enzymatic degradation. Various crosslinking agents have been used in fixing biological tissue. These crosslinking agents are mostly synthetic chemicals such as formaldehyde, glutaraldehyde, dialdehyde starch, glyceraldehydes, cyanamide, diimides, diisocyanates, dimethyl adipimidate, carbodiimide, and epoxy compound. However, these chemicals are all highly cytotoxic which may impair the biocompatibility of biological tissue. Of these, glutaraldehyde is known to have allergenic properties, causing occupational dermatitis and is cytotoxic at concentrations greater than 10–25 ppm and as low as 3 ppm in tissue culture. It is therefore desirable to provide a crosslinking agent (synonymous to a crosslinking reagent) suitable for use in biomedical applications that is within acceptable cytotoxicity and that forms stable and biocompatible crosslinked products.

An example of a genipin-crosslinked heart valve is reported by Sung et al., a co-inventor of the present invention, (Journal of Thoracic and Cardiovascular Surgery vol. 122, pp. 1208–1218. 2001) entitled Reconstruction of the right ventricular outflow tract with a bovine jugular vein graft fixed with a naturally occurring crosslinking agent (genipin) in a canine model, entire contents of which are incorporated herein by reference. Sung et al. herein discloses genipin and its crosslinking ability to a collagen-containing biological tissue heart valve.

To achieve this goal, a naturally occurring crosslinking agent (genipin) has been used to fix biological tissue. The application Ser. No. 09/297,808 filed Nov. 04, 1997, entitled "Chemical modification of biomedical materials with genipin" and its PCT counterpart, WO 98/19718, are incorporated and cited herein by reference. The cytotoxicity of genipin was previously studied in vitro using 3T3 fibroblasts, indicating that genipin is substantially less cytotoxic than glutaraldehyde (Sung H W et al., J Biomater Sci Polymer Edn 1999;10:63–78). Additionally, the genotoxicity of genipin was tested in vitro using Chinese hamster ovary (CHO-K1) cells, suggesting that genipin does not cause clastogenic response in CHO-K1 cells (Tsai C C et al., J Biomed Mater Res 2000;52:58–65), incorporated herein by reference. A biological material (including collagen-containing or chitosan-containing substrate) treated with genipin resulting in acceptable cytotoxicity is a first requirement to biomedical applications.

In a co-pending application by one inventor of the present application, U.S. patent application Ser. No. 10/067,130 filed Feb. 4, 2002, now U.S. Pat. No. 6,545,042, entitled Acellular Biological Material Chemically Treated with Genipin, entire contents of which are incorporated herein by reference, discloses an acellular tissue providing a natural microenvironment for host cell migration to accelerate tissue regeneration. The genipin-treated biological biomaterial has reduced antigenicity and immunogenicity.

Restenosis in Angioplasty and Stenting

Atherosclerosis causes a partial blockage of the blood vessels that supply the heart with nutrients. Atherosclerotic blockage of blood vessels often leads to hypertension, ischemic injury, stroke, or myocardial infarction. Typically angioplasty and/or stenting is a remedy for such a disease, however, restenosis does occur in 30–40 percent patients resulting from intimal smooth muscle cell hyperplasia. The underlying cause of the intimal smooth muscle cell hyperplasia is mainly vascular smooth muscle injury and disruption of the endothelial lining.

Vascular injury causing intimal thickening can be from mechanical injuries due to angioplasty and/or stenting. Intimal thickening following balloon catheter injury has been studied in animals as a model for arterial restenosis that occurs in human patients following balloon angioplasty. Injury is followed by a proliferation of the medial smooth muscle cells, after which many of them migrate into the intima through fenestrate in the internal elastic lamina and proliferate to form a neointimal lesion.

Vascular stenosis can be detected and evaluated using angiographic or sonographic imaging techniques and is often treated by percutaneous transluminal coronary angioplasty (balloon catheterization). Within a few months following angioplasty, however, the blood flow is reduced in approximately 30–40 percent of these patients as a result of restenosis caused by a response to mechanical vascular injury suffered during the angioplasty or stenting procedure, as described above.

In an attempt to prevent restenosis or reduce intimal smooth muscle cell proliferation following angioplasty, numerous pharmaceutical agents have been employed clinically, concurrent with or following angioplasty. Most pharmaceutical agents employed in an attempt to prevent or reduce the extent of restenosis have been unsuccessful. The following list identifies several of the agents for which favorable clinical results have been reported: lovastatin; thromboxane $A_2$ synthetase inhibitors such as DP-1904; eicosapentanoic acid; ciprostene (a prostacyclin analog); trapidil (a platelet derived growth factor)]; angiotensin convening enzyme inhibitors; and low molecular weight heparin, entire contents of the above-referred drugs and their therapeutic effects are incorporated herein by reference. It is one aspect of the present invention to provide site-specific administration of the pharmaceutical agents disclosed in this invention to the injury site for effective therapy via a genipin-crosslinked collagen-containing or chitosan-containing biological carrier.

Many compounds have been evaluated in a standard animal model. The immunosuppressive agent cyclosporin A has been evaluated and has produced conflicting results. Jonasson reported that cyclosporin A caused an inhibition of the intimal proliferative lesion following arterial balloon catheterization in vivo, but did not inhibit smooth muscle cell proliferation in vitro. It was reported that when de-endothelialized rabbits were treated with cyclosporin A, no significant reduction of intimal proliferation was observed in vivo. Additionally, intimal accumulations of foamy macrophages, together with a number of vacuolated smooth muscle cells in the region adjacent to the internal elastic lamina were observed, indicating that cyclosporin A may modify and enhance lesions that form at the sites of arterial injury.

Morris et al. in U.S. Pat. No. 5,516,781 disclosed Rapamycin, a macrocyclic triene antibiotic produced by Streptomyces hygroscopicus that has been shown to prevent the formation of humoral (IgE-like) antibodies in response to an albumin allergic challenge, inhibit murine T-cell activation, prolong survival time of organ gratis in histoincompatible rodents, and inhibit transplantation rejection in mammals. Rapamycin blocks calcium-dependent, calcium-independent, cytokine-independent and constitutive T and B cell division at the G1-S interface. Rapamycin inhibits gamma-interferon production induced by Il-1 and also inhibits the gamma-interferon induced expression of membrane antigen. Arterial thickening following transplantation, known as CGA, is a limiting factor in graft survival that is caused by a chronic immunological response to the transplanted blood vessels by the transplant recipient's immune system.

Further, Morris et al. in U.S. Pat. No. 5,516,781 claims the invention is distinct from the use of rapamycin for preventing CGA, in that CGA does not involve injury to the recipients' own blood vessels; it is a rejection type response. The disclosed patent '781 is related to vascular injury to native blood vessels. The resulting intimal smooth muscle cell proliferation does not involve the immune system, but is growth factor mediated. For example, arterial intimal thickening after balloon catheter injury is believed to be caused by growth factor (PGDF, bFGF, TGFb, IL-1 and others)-induced smooth muscle cell proliferation and migration. The above-cited U.S. Pat. No. 5,516,781 is incorporated herein by reference.

In the past, polymer or plastic materials have been used as a carrier for depositing a drug or pharmaceutical agent onto the periphery of a stent to treat restenosis. Example is U.S. Pat. No. 5,886,016 to Hunter et al., entire contents of which are incorporated herein by reference. Hunter et al. discloses a method for treating a tumor excision site, comprising administering to a patient a composition comprising paclitaxel, or an analogue or derivative thereof, to the resection margin of a tumor subsequent to excision, such that the local recurrence of cancer and the formation of new blood vessels at said site is inhibited. The composition further comprises a polymer, wherein the polymer may comprise poly (caprolactone), poly (lactic acid), poly (ethylene-vinyl acetate), and poly (lactic-co-glycolic) acid.

In another example, Biocompatibles PC (phosphorylcholine by Biocompatibles, London, England) has been added as a drug carrier or surface modifier for treating tissue injury due to angioplasty and/or stenting. The technique comprises a hydrophobic component that aids in the initial adhesion and film-formation of the polymer onto the stainless steel stent substrate, and other groups allow cross-linking both within the polymer and with the stent surface to achieve firm anchorage. The coating is thus tenaciously adhered to the stent and can survive balloon expansion without damage. A therapeutic drug can be loaded within the coated substrate, such as phosphorylcholine.

Drugs are usually loaded, admixed or entrapped physically within the polymer framework for slow drug release. The plastic polymer which is suitable as a drug carrier may not be biocompatible, whereas some biocompatible plastic polymer may not be able to contain a specific drug and release drug in an effective timely amount for effective therapy. Therefore, there is a clinical need to have a biocompatible drug carrier that releases an effective quantity of drug over a period of time for prolonged therapeutic effects.

In accordance with the present invention there is provided genipin treated solidifiable collagen-containing or chitosan-containing biological material loaded with drug for implant and other surgical applications which have shown to exhibit many of the desired characteristics important for optimal therapeutic function. In particular, the crosslinked collagen-drug compound with drug slow release capability may be suitable as anti restenosis agent in treating atherosclerosis and other therapeutic applications.

SUMMARY OF THE INVENTION

In general, it is an object of the present invention to provide a biological substance configured and adapted for drug slow release. In one aspect of the present invention, the biological substance may be adhesively loaded onto a stent surface rendering the stent to slowly release drug from the biological substance. The "biological substance" is herein intended to mean a substance made of drug-containing biological material that is solidifiable upon change of environmental condition(s) and is biocompatible post-crosslinking with a crosslinker, such as genipin, epoxy compounds, dialdehyde starch, glutaraldehyde, or the like. The "biological material" is intended herein to mean collagen, gelatin, elastin, chitosan, NOCC (N, O, Carboxylmethyl Chitosan), and the like that could be crosslinked with a crosslinker (also known as a crosslinking agent).

In one embodiment, the process of preparing a biological substance comprises steps of loading drugs with the biological material, shaping the drug-containing biological material, followed by crosslinking with genipin. The genipin referred herein is broadly consisted of the naturally occurring compound as shown in FIG. 1 and its derivatives, analog, stereoisomers and mixtures thereof. In another embodiment, the drug-containing biological material is further coated, adhered or loaded onto a substrate before or after crosslinking with a crosslinker (such as genipin). The biological material is herein broadly generally referred to collagen, elastin, gelatin, chitosan, NOCC, the mixtures thereof, and derivates, analog and mixtures thereof. The biological material may be in a form or phase of solution, paste, gel, suspense, colloid or plasma that is solidifiable thereafter.

It is another object of the present invention to provide a method for drug slow release from a medical device comprising entrapping drug within a biological material crosslinked with genipin. The medical device can be a stent, a non-stent implant or prosthesis, or a percutaneous device such as a catheter, a wire, a cannula, an endoscopic instrument or the like for the intended drug slow release. In one embodiment, the non-stent implant may comprise annuloplasty rings, heart valve prostheses, orthopedic implants, dental implants, ophtalmology implants, cardiovascular implants, and cerebral implants.

It is a further object of the present invention to provide a method for drug slow release from an implant comprising chemically bonding ionically or covalently drug within a biological material crosslinked with genipin, wherein the drug has an amine or amino group branch. In one aspect of the present invention, the amine or amino group of the drug is reacted with the amino group of collagen through a crosslinker.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

The following detailed description is of the best presently contemplated modes of carrying out the invention. This description is not to be taken in a limiting sense, but is made merely for the purpose of illustrating general principles of embodiments of the invention.

Figure 1:
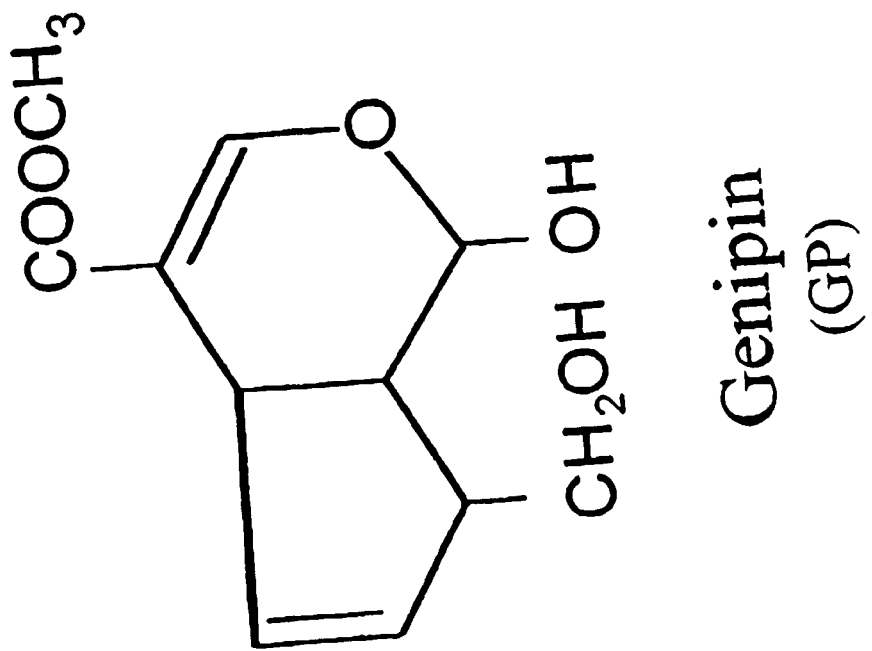
FIG. 1 is chemical structures of glutaraldehyde and genipin that are used in the chemical treatment examples of the current disclosure.
Figure 1:
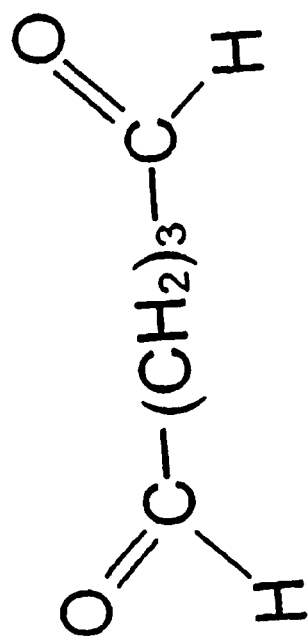

"Genipin" in this invention is meant to refer to the naturally occurring compound as shown in FIG. 1 and its derivatives, analog, stereoisomers and mixtures thereof.

"Crosslinking agent" is meant herein to indicate a chemical agent that could crosslink two molecules, such as formaldehyde, glutaraldehyde, dialdehyde starch, glyceraldehydes, cyanamide, diimides, diisocyanates, dimethyl adipimidate, carbodiimide, and epoxy compound.

"Biological material" is herein meant to refer to collagen extract, soluble collagen, elastin, gelatin, chitosan, chitosan-containing and other collagen-containing biological material. For a preferred aspect of the present invention, the biological material is meant to indicate a solidifiable biological substrate comprising at least a genipin-crosslinkable functional group, such as amino group or the like.

A "biological implant" refers to a biomedical device which is inserted into, or grafted onto, bodily tissue to remain for a period of time, such as an extended-release drug delivery device, vascular or skin graft, or orthopedic prosthesis, such as bone, ligament, tendon, cartilage, and muscle.

"Drug" in this invention is meant to broadly refer to a chemical or biological molecule(s) providing a therapeutic, diagnostic, or prophylactic effect in vivo. "Drug" may comprise, but not limited to, synthetic chemicals, biotechnology-derived molecules, herbs, health food and/or alternate medicines.

The "biological substance" is herein intended to mean a substance made of drug-containing biological material that is solidifiable upon change of environmental condition(s) and is biocompatible after being crosslinked with a crosslinker, such as genipin, epoxy compounds, dialdehyde starch, glutaraldehyde, formaldehyde, dimethyl adipimidate, carbodiimide, or the like.

The "biological material" is intended herein to mean collagen, gelatin, elastin, chitosan, NOCC (N, O, Carboxylmethyl Chitosan), chitosan-containing material, collagen-containing material, and the like that could be crosslinked with a crosslinker (also known as a crosslinking agent).

Preparation and Properties of Genipin

Figure 2A:
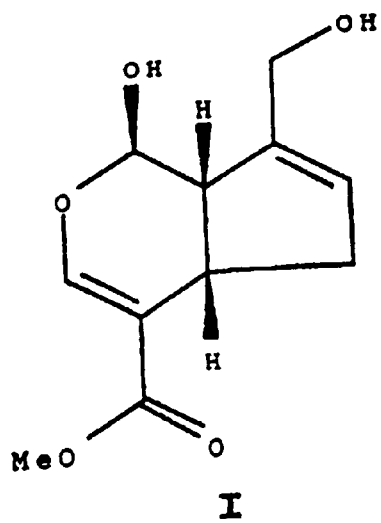
FIG. 2A is an iridoid glycoside present in fruits of Gardenia jasmindides Ellis (Structure I).
Figure 2B:
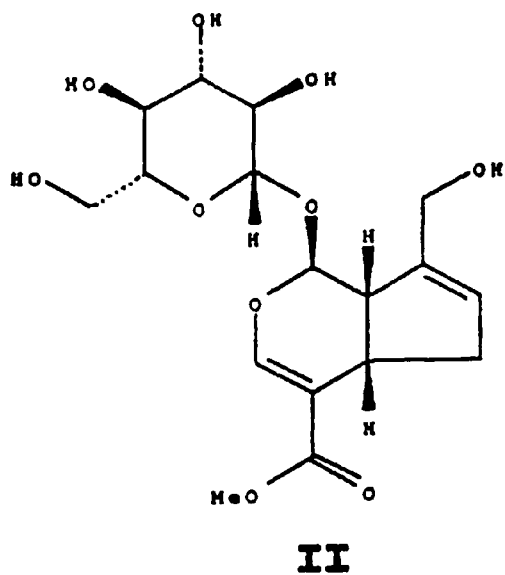
FIG. 2B is a parent compound geniposide (Structure II) from which genipin is derived.

Genipin, shown in Structure I of FIG. 2A, is an iridoid glycoside present in fruits (Gardenia jasmindides Ellis). It may be obtained from the parent compound geniposide, Structure II (FIG. 2B), which may be isolated from natural sources as described in elsewhere. Genipin, the aglycone of geniposide, may be prepared from the latter by oxidation followed by reduction and hydrolysis or by enzymatic hydrolysis. Alternatively, racemic genipin may be prepared synthetically. Although Structure I shows the natural configuration of genipin, any stereoisomer or mixture of stereoisomers of genipin may be used as a crosslinking reagent, in accordance with the present invention.

Genipin has a low acute toxicity, with $LD_{50}$ i.v. 382 mg/k in mice. It is therefore much less toxic than glutaraldehyde and many other commonly used synthetic crosslinking reagents. As described below, genipin is shown to be an effective crosslinking agent for treatment of biological materials intended for in vivo biomedical applications, such as prostheses and other implants, wound dressings, and substitutes.

It is one object of the present invention to provide a drug-collagen-genipin and/or drug-chitosan-genipin compound that is loaded onto the periphery of a cardiovascular stent enabling drug slow-release to the surrounding tissue, to the lumen of the bodily cavity.

Previously, Chang in U.S. Pat. No. 5,929,038 discloses a method for treating hepatitis B viral infection with an iridoid compound of a general formula containing a six-member hydrocarbon ring sharing with one common bondage of a five-member hydrocarbon ring. Further, Moon et al. in U.S. Pat. No. 6,162,826 and U.S. Pat. No. 6,262,083 discloses genipin derivatives having anti hepatitis B virus activity and liver protection activity. All of which three aforementioned patents are incorporated herein by reference. The teachings of these patents do not disclose preparing tissue/device with scaffolds or collagen matrix with desirable porosity for use in tissue engineering, wherein the raw material source for tissue engineering is chemically modified by genipin, genipin derivatives or its analog with acceptably minimal cytotoxicity.

Kyogoku et al. in U.S. Pat. No. 5,037,664, U.S. Pat. No. 5,270,446, and EP 0366998, entire contents of all three being incorporated herein by reference, teach the crosslinking of amino group containing compounds with genipin and the crosslinking of genipin with chitosan. They also teach the crosslinking of iridoid compounds with proteins which can be vegetable, animal (collagen, gelatin) or microbial origin. However, they do not teach loading drug onto a collagen-containing biological material crosslinked with genipin as biocompatible drug carriers for drug slow-release.

Smith in U.S. Pat. No. 5,322,935, incorporated herein by reference in its entirety, teaches the crosslinking of chitosan polymers and then further crosslinking again with covalent crosslinking agents like glutaraldehyde. Smith, however, does not teach loading drug onto a chitosan-containing biological material crosslinked with genipin as biocompatible drug carriers for drug slow-release.

Noishiki et al. in U.S. Pat. No. 4,806,595 discloses a tissue treatment method by a crosslinking agent, polyepoxy compounds. Collagens used in that patent include an insoluble collagen, a soluble collagen, an atelocollagen prepared by removing telopeptides on the collagen molecule terminus using protease other than collagenase, a chemically modified collagen obtained by succinylation or esterification of above-described collagens, a collagen derivative such as gelatin, a polypeptide obtained by hydrolysis of collagen, and a natural collagen present in natural tissue (ureter, blood vessel, pericardium, heart valve, etc.) The Noishiki et al. patent is incorporated herein by reference. "Biological material" in the present invention is additionally used herein to refer to the above-mentioned collagen, collagen species, collagen in natural tissue, and collagen in a biological implant preform that are shapeable and solidifiable.

Voytik-Harbin et al. in U.S. Pat. No. 6,264,992 discloses submucosa as a growth substrate for cells. More particularly, the submucosa is enzymatically digested and gelled to form a shape retaining gel matrix suitable for inducing cell proliferation and growth both in vivo and in vitro. The Voytik-Harbin et al. patent is incorporated herein by reference. Biological material, additionally including submucosa, that is chemically modified or treated by genipin or other crosslinker of the present invention may serve as a shapeable raw material for making a biological substance adapted for inducing cell proliferation and ingrowth, but also resisting enzymatic degradation, both in vivo and in vitro. In a further aspect of the present invention, drug is loaded with submucosa biological material and crosslinked with a crosslinker, such as genipin.

Cook et al. in U.S. Pat. No. 6,206,931 discloses a graft prosthesis material including a purified, collagen-based matrix structure removed from a submucosa tissue source, wherein the submucosa tissue source is purified by disinfection and removal steps to deactivate and remove contaminants. The Cook et al. patent is incorporated herein by reference. Similarly, a collagen-based matrix structure, also known as "biological material" in this disclosure, may serve as a biomaterial adapted for medical device use after chemical modification by genipin of the present invention.

Levene et al. in U.S. Pat. No. 6,103,255 discloses a porous polymer scaffold for tissue engineering, whereby the scaffold is characterized by a substantially continuous solid phase, having a highly interconnected bimodal distribution of open pore sizes. The Levene et al. patent is incorporated herein by reference. The present invention discloses biological scaffold material by acellular process and acidic/enzymatic treatment adapted for tissue engineering. Additional benefits of genipin tissue treatment for reduced antigenicity, reduced cytotoxicity and enhanced biodurability on a drug-containing biological substance are disclosed in the present invention.

Several disadvantages are associated with the currently available technology. First, the prior art teaches collagen or chitosan in drug delivery application without suitable crosslinkage. The drug within collagen or chitosan matrix may tend to leach out in a short period of time because of no crosslinked barriers surrounding the drug. Another prior art teaches crosslinked collagen or chitosan without drug slow-release properties. It is essential that drug is appropriately loaded within collagen or chitosan before the drug-containing collagen/chitosan is crosslinked enabling drug slow-release. Therefore, even if the two afore-mentioned prior arts were to be combined in a conventional manner, the combination would not show all of the novel physical feature and unexpected results of the present invention.

Collapen-Drug-Genipin Compound

In one embodiment of the present invention, it is disclosed that a method for treating tissue of a patient comprising, in combination, loading a solidifiable drug-containing biological material onto a medical device, solidifying the drug-containing biological material, chemically treating the drug-containing biological material with a crosslinking agent, and delivering said medical device to a target tissue for treating the tissue. The collagen-drug-genipin compound or the chitosan-drug-genipin compound and methods of manufacture as disclosed and supported in the below examples produce new and unexpected results and hence are unobvious from the prior art. The medical device can be a stent, a non-stent implant or prosthesis, or a percutaneous device such as a catheter, a wire, a cannula, an endoscopic instrument or the like for the intended drug slow release. In one aspect, the non-stent implant may comprise annuloplasty rings, heart valve prostheses, orthopedic implants, dental implants, ophthalmology implants, cardiovascular implants, and cerebral implants. In another aspect of the present invention, the target tissue may comprise vulnerable plaque, atherosclerotic plaque, tumor or cancer, brain tissue, vascular vessel or tissue, orthopedic tissue, ophthalmology tissue or the like.

In another embodiment of the present invention, it is disclosed a biological substance for treating tissue of a patient with drug slow release, wherein the biological substance is made of drug-containing biological material that is solidifiable upon change of environmental condition(s) and is biocompatible after crosslinked with a crosslinker, such as genipin, epoxy compounds, dialdehyde starch, dimethyl adipimidate, carbodiimide, glutaraldehyde, or the like.

In still another embodiment of the present invention, it is disclosed that a method for treating tissue of a patient comprising, in combination, mixing a drug with a solidifiable biological material, chemically treating the drug with the biological material with a crosslinking agent, loading the solidifiable drug-containing biological material onto a medical device, and solidify the drug-containing biological material.

It is some aspect of the present invention that the method may further comprise chemically linking the drug with the biological material through a crosslinker, wherein the drug comprises at least a crosslinkable functional group; for example, an amino group.

It is a further aspect of the present invention to provide a method for treating vascular restenosis comprising, in combination, loading a solidifiable drug-containing biological material onto a medical device, solidifying the drug-containing biological material, chemically treating the drug-containing biological material with a crosslinking agent, and delivering said medical device to a vascular restenosis site for treating the vascular restenosis.

Drug for use in Collagen-Drug-Genipin Compound

Straub et al. in U.S. Pat. No. 6,395,300 discloses a wide variety of drugs that are useful in the methods and compositions described herein, entire contents of which, including a variety of drugs, are incorporated herein by reference. Drugs contemplated for use in the compositions described in U.S. Pat. No. 6,395,300 and herein disclosed include the following categories and examples of drugs and alternative forms of these drugs such as alternative salt forms, free acid forms, free base forms, and hydrates:

analgesics/antipyretics. (e.g., aspirin, acetaminophen, ibuprofen, naproxen sodium, buprenorphine, propoxyphene hydrochloride, propoxyphene napsylate, meperidine hydrochloride, hydromorphone hydrochloide, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, diphenhydramine citrate, methotrimeprazine, cinnamedrine hydrochloride, and meprobamate);

antiasthamatics (e.g., ketotifen and traxanox);

antibiotics (e.g., neomycin, streptomycin, chloramphenicol, cephalosporin, ampicillin, penicillin, tetracycline, and ciprofloxacin);

antidepressants (e.g., nefopam, oxypertine, doxepin, amoxapine, trazodone, amitriptyline, maprotiline, phenelzine, desipramine, nortriptyline, tranylcypromine, fluoxetine, doxepin, imipramine, imipramine pamoate, isocarboxazid, trimipramine, and protriptyline);

antidiabetics (e.g., biguanides and sulfonylurea derivatives);

antifungal agents (e.g., griseofulvin, ketoconazole, itraconizole, amphotericin B, nystatin, and candicidin);

antihypertensive agents (e.g., propanolol, propafenone, oxyprenolol, nifedipine, reserpine, trimethaphan, phenoxybenzamine, pargyline hydrochloride, deserpidine, diazoxide, guanethidine monosulfate, minoxidil, rescinnamine, sodium nitroprusside, rauwolfia serpentina, alseroxylon, and phentolamine);

anti-inflammatories (e.g., (non-steroidal) indomethacin, ketoprofen, flurbiprofen, naproxen, ibuprofen, ramifenazone, piroxicam, (steroidal) cortisone, dexamethasone, fluazacort, celecoxib, rofecoxib, hydrocortisone, prednisolone, and prednisone);

antineoplastics (e.g., cyclophosphamide, actinomycin, bleomycin, daunorubicin, doxorubicin, epirubicin, mitomycin, methotrexate, fluorouracil, carboplatin, carmustine (BCNU), methyl-CCNU, cisplatin, etoposide, camptothecin and derivatives thereof, phenesterine, paclitaxel and derivatives thereof, docetaxel and derivatives thereof, vinblastine, vincristine, tamoxifen, and piposulfan);

antianxiety agents (e.g., lorazepam, buspirone, prazepam, chlordiazepoxide, oxazepam, clorazepate dipotassium, diazepam, hydroxyzine pamoate, hydroxyzine hydrochloride, alprazolam, droperidol, halazepam, chlormezanone, and dantrolene);

immunosuppressive agents (e.g., cyclosporine, azathioprine, mizoribine, and FK506 (tacrolimus));

antimigraine agents (e.g., ergotamine, propanolol, isometheptene mucate, and dichloralphenazone);

sedatives/hypnotics (e.g., barbiturates such as pentobarbital, pentobarbital, and secobarbital; and benzodiazapines such as flurazepam hydrochloride, triazolam, and midazolam);

antianginal agents (e.g., beta-adrenergic blockers; calcium channel blockers such as nifedipine, and diltiazem; and nitrates such as nitroglycerin, isosorbide dinitrate, pentearythritol tetranitrate, and erythrityl tetranitrate);

antipsychotic agents (e.g., haloperidol, loxapine succinate, loxapine hydrochloride, thioridazine, thioridazine hydrochloride, thiothixene, fluphenazine, fluphenazine decanoate, fluphenazine enanthate, trifluoperazine, chlorpromazine, perphenazine, lithium citrate, and prochlorperazine);

antimanic agents (e.g., lithium carbonate);

antiarrhythmics (e.g., bretylium tosylate, esmolol, verapamil, amiodarone, encainide, digoxin, digitoxin, mexiletine, disopyramide phosphate, procainamide, quinidine sulfate, quinidine gluconate, quinidine polygalacturonate, flecainide acetate, tocainide, and lidocaine);

antiarthritic agents (e.g., phenylbutazone, sulindac, penicillanine, salsalate, piroxicam, azathioprine, indomethacin, meclofenamate, gold sodium thiomalate, ketoprofen, auranofin, aurothioglucose, and tolmetin sodium);

antigout agents (e.g., colchicine, and allopurinol);

anticoagulants (e.g., heparin, heparin sodium, and warfarin sodium);

thrombolytic agents (e.g., urokinase, streptokinase, and alteplase);

antifibrinolytic agents (e.g., aminocaproic acid);

hemorheologic agents (e.g., pentoxifylline);

antiplatelet agents (e.g., aspirin);

anticonvulsants (e.g., valproic acid, divalproex sodium, phenytoin, phenytoin sodium, clonazepam, primidone, phenobarbitol, carbamazepine, amobarbital sodium, methsuximide, metharbital, mephobarbital, mephenytoin, phensuximide, paramethadione, ethotoin, phenacemide, secobarbitol sodium, clorazepate dipotassium, and trimethadione);

antiparkinson agents (e.g., ethosuximide);

antihistamines/antipruritics (e.g., hydroxyzine, diphenhydramine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorphenirarnine maleate, methdilazine, and);

agents useful for calcium regulation (e.g., calcitonin, and parathyroid hormone);

antibacterial agents (e.g., amikacin sulfate, aztreonam, chloramphenicol, chloramphenicol palirtate, ciprofloxacin, clindamycin, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, and colistin sulfate);

antiviral agents (e.g., interferon alpha, beta or gamma, zidovudine, amantadine hydrochloride, ribavirin, and acyclovir);

antimicrobials (e.g., cephalosporins such as cefazolin sodium, cephradine, cefaclor, cephapirin sodium, ceftizoxime sodium, cefoperazone sodium, cefotetan disodium, cefuroxime e azotil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, and cefuroxime sodium; penicillins such as ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, and nafcillin sodium; erythromycins such as erythromycin ethylsuccinate, erythromycin, erythromycin estolate, erythromycin lactobionate, erythromycin stearate, and erythromycin ethylsuccinate; and tetracyclines such as tetracycline hydrochloride, doxycycline hyclate, and minocycline hydrochloride, azithromycin, clarithromycin);

anti-infectives (e.g., GM-CSF);

bronchodilators (e.g., sympathomimetics such as epinephrine hydrochloride, metaproterenol sulfate, terbutaline sulfate, isoetharine, isoetharine mesylate, isoetharine hydrochloride, albuterol sulfate, albuterol, bitolterolmesylate, isoproterenol hydrochloride, terbutaline sulfate, epinephrine bitartrate, metaproterenol sulfate, epinephrine, and epinephrine bitartrate; anticholinergic agents such as ipratropium bromide; xanthines such as aminophylline, dyphylline, metaproterenol sulfate, and aminophylline; mast cell stabilizers such as cromolyn sodium; inhalant corticosteroids such as beclomethasone dipropionate (BDP), and beclomethasone dipropionate monohydrate; salbutamol; ipratropium bromide; budesonide; ketotifen; salmeterol; xinafoate; terbutaline sulfate; triamcinolone; theophylline; nedocromil sodium; metaproterenol sulfate; albuterol; flunisolide; fluticasone proprionate;

steroidal compounds and hormones (e.g., androgens such as danazol, testosterone cypionate, fluoxymesterone, ethyltestosterone, testosterone enathate, methyltestosterone, fluoxymesterone, and testosterone cypionate; estrogens such as estradiol, estropipate, and conjugated estrogens; progestins such as methoxyprogesterone acetate, and norethindrone acetate; corticosteroids such as triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate, methylprednisolone sodium succinate, hydrocortisone sodium succinate, triamcinolone hexacetonide, hydrocortisone, hydrocortisone cypionate, prednisolone, fludrocortisone acetate, paramethasone acetate, prednisolone tebutate, prednisolone acetate, prednisolone sodium phosphate, and hydrocortisone sodium succinate; and thyroid hormones such as levothyroxine sodium);

hypoglycemic agents (e.g., human insulin, purified beef insulin, purified pork insulin, glyburide, chlorpropamide, glipizide, tolbutarnide, and tolazamide);

hypolipidemic agents (e.g., clofibrate, dextrothyroxine sodium, probucol, pravastitin, atorvastatin, lovastatin, and niacin);

proteins (e.g., DNase, alginase, superoxide dismutase, and lipase);

nucleic acids (e.g., sense or anti-sense nucleic acids encoding any therapeutically useful protein, including any of the proteins described herein);

agents useful for erythropoiesis stimulation (e.g., erythropoietin);

antiulcer/antireflux agents (e.g., famotidine, cimetidine, and ranitidine hydrochloride);

antinauseants/antiemetics (e.g., meclizine hydrochloride, nabilone, prochlorperazine, dimenhydrinate, promethazine hydrochloride, thiethylperazine, and scopolamine);

as well as other drugs useful in the compositions and methods described herein include mitotane, halonitrosoureas, anthrocyclines, ellipticine, ceftriaxone, ketoconazole, ceftazidime, oxaprozin, albuterol, valacyclovir, urofollitropin, famciclovir, flutamide, enalapril, mefformin, itraconazole, buspirone, gabapentin, fosinopril, tramadol, acarbose, lorazepan, follitropin, glipizide, omeprazole, fluoxetine, lisinopril, tramsdol, levofloxacin, zafirlukast, interferon, growth hormone, interleukin, erythropoietin, granulocyte stimulating factor, nizatidine, bupropion, perindopril, erbumine, adenosine, alendronate, alprostadil, benazepril, betaxolol, bleomycin sulfate, dexfenfluramine, diltiazem, fentanyl, flecainid, gemcitabine, glatiramer acetate, granisetron, lamivudine, mangafodipir trisodium, mesalamine, metoprolol fumarate, metronidazole, miglitol, moexipril, monteleukast, octreotide acetate, olopatadine, paricalcitol, somatropin, sumatriptan succinate, tacrine, verapamil, nabumetone, trovafloxacin, dolasetron, zidovudine, finasteride, tobramycin, isradipine, tolcapone, enoxaparin, fluconazole, lansoprazole, terbinafine, pamidronate, didanosine, diclofenac, cisapride, venlafaxine, troglitazone, fluvastatin, losartan, imiglucerase, donepezil, olanzapine, valsartan, fexofenadine, calcitonin, and ipratropium bromide. These drugs are generally considered to be water soluble.

Preferred drugs useful in the present invention may include albuterol, adapalene, doxazosin mesylate, mometasone furoate, ursodiol, amphotericin, enalapril maleate, felodipine, nefazodone hydrochloride, valrubicin, albendazole, conjugated estrogens, medroxyprogesterone acetate, nicardipine hydrochloride, zolpidem tartrate, amlodipine besylate, ethinyl estradiol, omeprazole, rubitecan, amlodipine besylate/benazepril hydrochloride, etodolac, paroxetine hydrochloride, paclitaxel, atovaquone, felodipine, podofilox, paricalcitol, betamethasone dipropionate, fentanyl, pramipexole dihydrochloride, Vitamin $D_3$ and related analogues, finasteride, quetiapine fumarate, alprostadil, candesartan, cilexetil, fluconazole, ritonavir, busulfan, carbamazepine, flumazenil, risperidone, carbemazepine, carbidopa, levodopa, ganciclovir, saquinavir, amprenavir, carboplatin, glyburide, sertraline hydrochloride, rofecoxib carvedilol, halobetasolproprionate, sildenafil citrate, celecoxib, chlorthalidone, imiquimod, simvastatin, citalopram, ciprofloxacin, irinotecan hydrochloride, sparfloxacin, efavirenz, cisapride monohydrate, lansoprazole, tamsulosin hydrochloride, mofafinil, clarithromycin, letrozole, terbinafine hydrochloride, rosiglitazone maleate, diclofenac sodium, lomefloxacin hydrochloride, tirofiban hydrochloride, telmisartan, diazepam, loratadine, toremifene citrate, thalidomide, dinoprostone, mefloquine hydrochloride, trandolapril, docetaxel, mitoxantrone hydrochloride, tretinoin, etodolac, triamcinolone acetate, estradiol, ursodiol, nelfinavir mesylate, indinavir, beclomethasone dipropionate, oxaprozin, flutamide, famotidine, nifedipine, prednisone, cefuroxime, lorazepam, digoxin, lovastatin, griseofulvin, naproxen, ibuprofen, isotretinoin, tamoxifen citrate, nimodipine, amiodarone, and alprazolam.

Specific non-limiting examples of some drugs that fall under the above categories include paclitaxel, docetaxel and derivatives, epothilones, nitric oxide release agents, heparin, aspirin, coumadin, PPACK, hirudin, polypeptide from angiostatin and endostatin, methotrexate, 5-fluorouracil, estradiol, P-selectin Glycoprotein ligand-1 chimera, abciximab, exochelin, eleutherobin and sarcodictyin, fludarabine, sirolimus, tranilast, VEGF, transforming growth factor (TGF)-beta, Insulin-like growth factor (IGF), platelet derived growth factor (PDGF), fibroblast growth factor (FGF), RGD peptide, beta or gamma ray emitter (radioactive) agents, and dexamethasone, tacrolimus, actinomycin-D, batimastat etc.

In some aspect of the present invention, the drug may broadly comprise, but not limited to, synthetic chemicals, biotechnology-derived molecules, herbs, health food, extracts, and/or alternate medicines; for example, including allicin and its corresponding garlic extract, ginsenosides and the corresponding ginseng extract, flavone/terpene lactone and the corresponding ginkgo biloba extract, glycyrrhetinic acid and the corresponding licorice extract, and polyphenol/proanthocyanides and the corresponding grape seed extract.

In the present invention, the terms "crosslinking", "fixation", "chemical modification", and "chemical treatment" for tissue are used interchangeably.

FIG. 1 shows chemical structures of glutaraldehyde and genipin that are used in the chemical treatment examples of the current disclosure. Other crosslink agents may equally be applicable for collagen-drug-genipin and/or chitosan-drug-genipin compound disclosed herein.

Other than genipin and glutaraldehyde, the crosslinking agent that may be used in chemical treatment of the present invention may include formaldehyde, dialdehyde starch, glyceraldehydes, cyanamide, diimides, diisocyanates, dimethyl adipimidate, carbodiimide, and epoxy compound.

Figure 3:
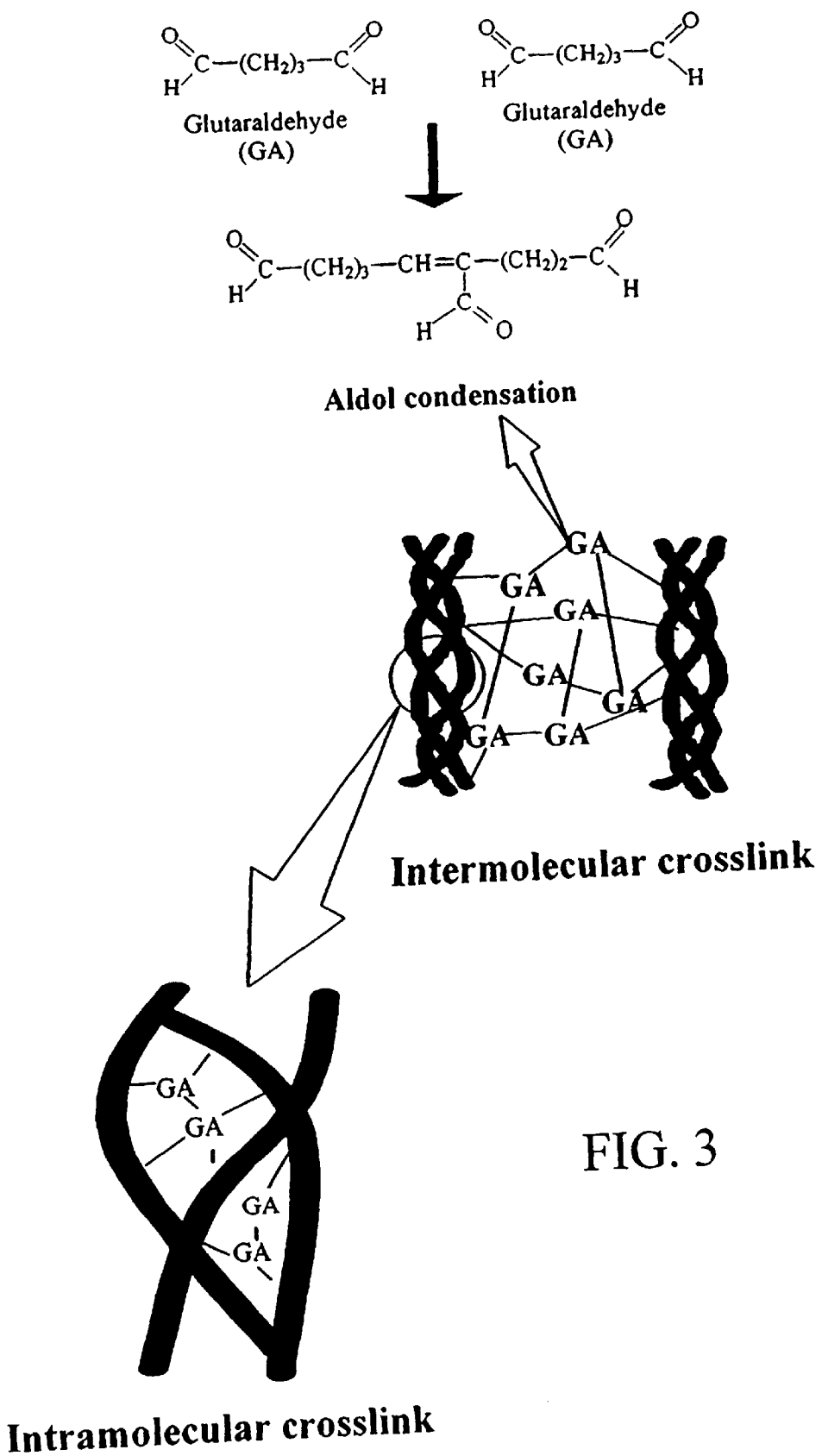
FIG. 3 is a proposed crosslinking mechanism for a crosslinker, glutardehyde (GA) with collagen intermolecularly and/or intramolecularly.

FIG. 3 shows a proposed crosslinking mechanism for a crosslinker, glutaraldehyde (GA) with collagen intermolecularly and/or intramolecularly.

Figure 4A:
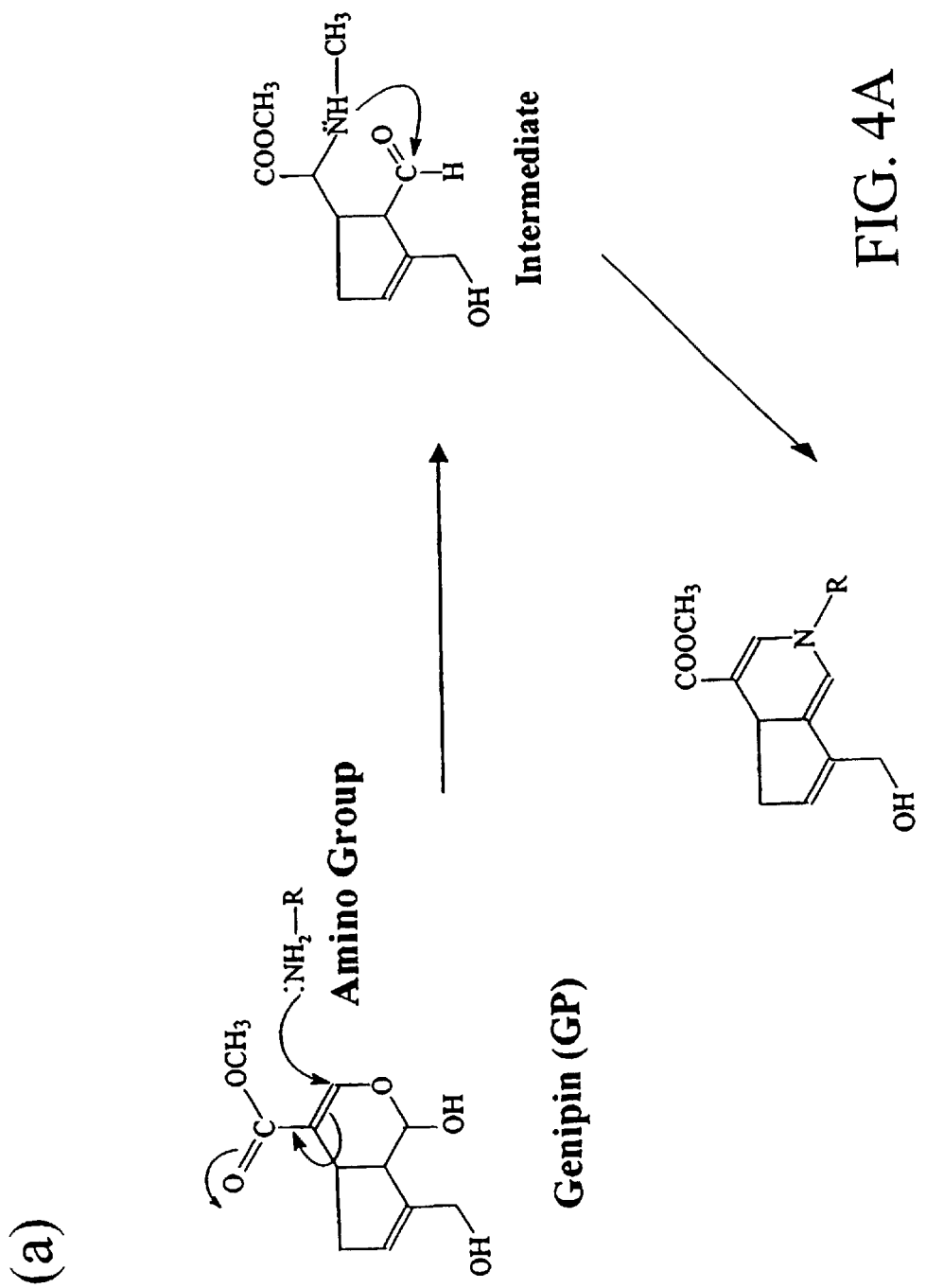
FIG. 4A is a proposed reaction mechanism between genipin and an amino group of a reactant, including collagen or certain type of drug of the present invention.
Figure 4B:
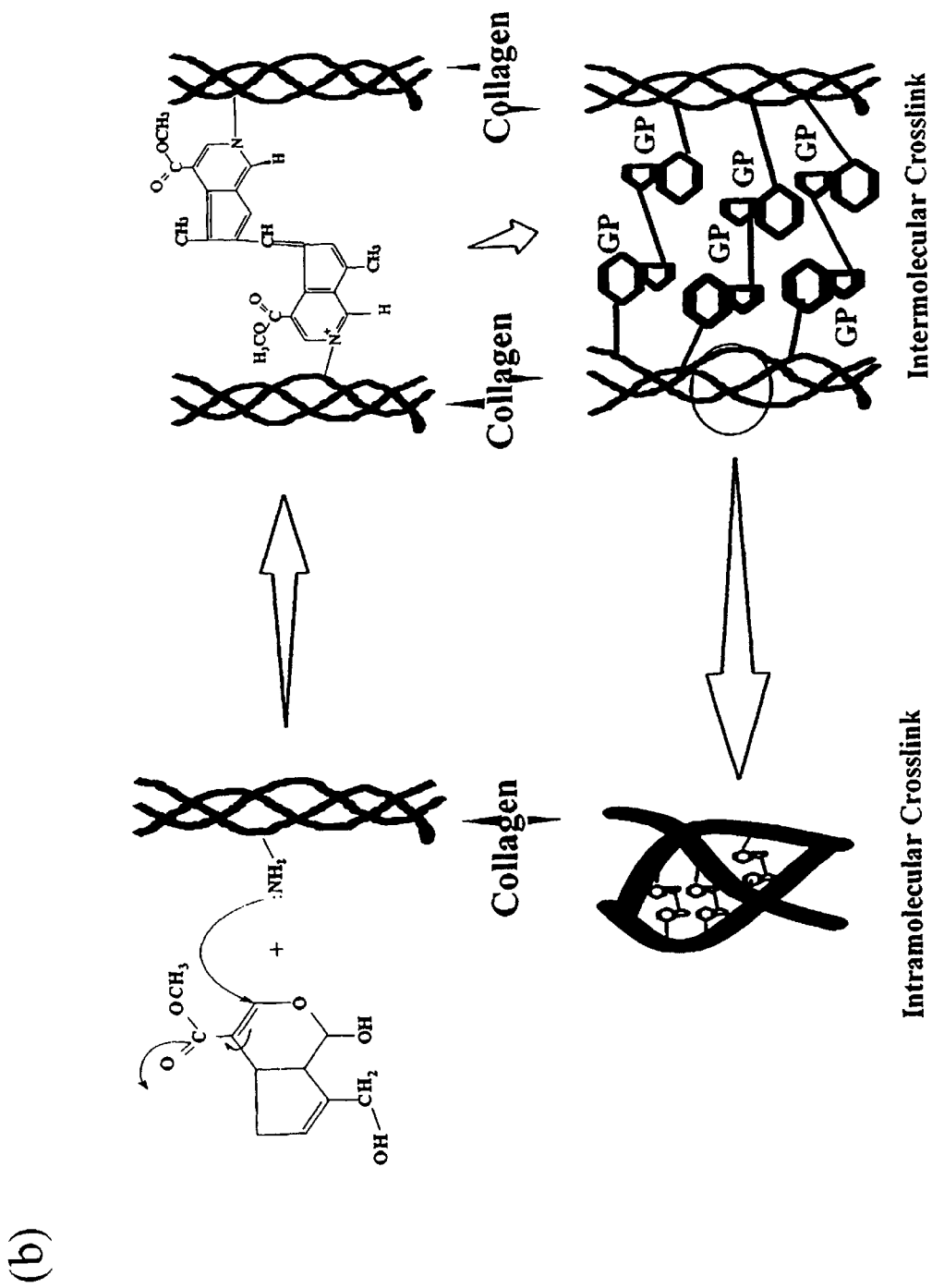
FIG. 4B is a proposed crosslinking mechanism for a crosslinker, genipin (GP) with collagen intermolecularly and/or intramolecularly.

FIG. 4A shows a proposed reaction mechanism between genipin and an amino group of a reactant, including collagen or certain type of drug of the present invention, while FIG. 4B shows a proposed crosslinking mechanism for a crosslinker, genipin (GP) with collagen intennolecularly and/or intramolecularly.

Figure 5:
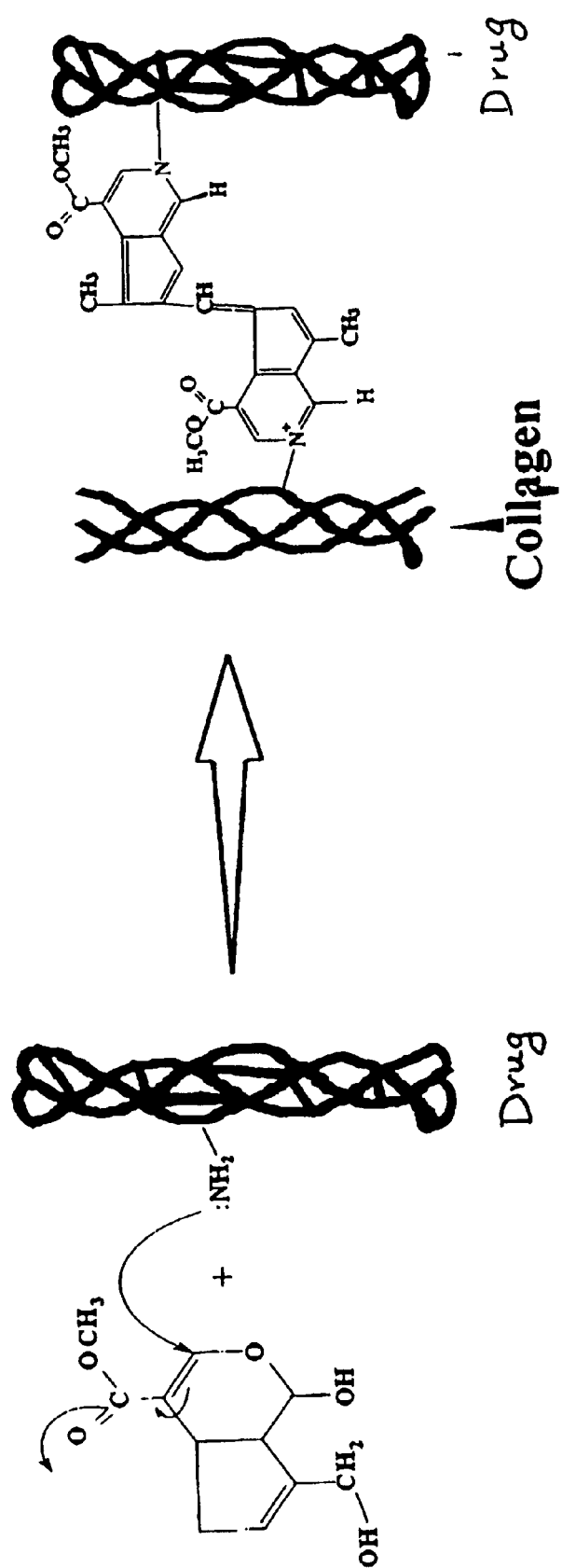
FIG. 5 is a schematic illustration for genipin to crosslink an amino-containing collagen and an amino-containing drug.

FIG. 5 is a schematic illustration for genipin to crosslink an amino-containing collagen and an amino-containing drug. It is also conceivable for a crosslinker, such as genipin to link an amine-containing substrate and an amino-containing drug. An example of amine-containing substrate is polyurethane and the like.

Glutaraldehyde Crosslinking

Glutaraldehyde has been used extensively as a crosslinking agent for fixing biologic tissues. By means of its aldehyde functional groups, glutaraldehyde reacts primarily with the $\epsilon$-amino groups of lysyl or hydroxylysyl residues within biologic tissues. The mechanism of fixation of biologic tissues or biologic matrix with glutaraldehyde can be found elsewhere. Polymerization of glutaraldehyde molecules in aqueous solution with observable reductions in free aldehyde have been reported previously (Nimni M E et al. in Nimni M E, editor. COLLAGEN. Vol. III. Boca Raton (Fla.); CRC Press 1998. pp. 1–38). In polymerization the aldehyde functional groups of 2 glutaraldehyde molecules may undergo an aldol condensation (FIG. 3). With glutaraldehyde polymerization, subsequent to fixation, a network crosslinking structure could conceivably be created intramolecularly and intermolecularly within collagen fibers (FIG.3).

It is conceivable that a substance (for example, a drug) having an amine or amino functional group may react with glutaraldehyde as illustrated above. By combining collagen, glutaraldehyde and a drug having an amine or amino group, the crosslinked compound may link collagen to the drug via glutaraldehyde as a crosslinker.

Crosslinking of a Polymer Having an Amine Group

Several biocompatible plastic polymers or synthetic polymers have one or more amine group in their chemical structures. The amine group may become reactive toward a crosslinker, such as glutaraldehyde, genipin or epoxy compounds. Therefore, it is conceivable that by combining a polymer having an amine group, glutaraldehyde and a drug having at least an amine or amino group, the crosslinked compound may have the polymer linked to the drug via glutaraldehyde as a crosslinker. Other crosslinkers are also applicable.

Genipin Crosslinking

It was found by Sung H W (Biomaterials 1999;20:1759–72) that genipin can react with the free amino groups of lysine, hydroxylysine, or arginine residues within biologic tissues. A prior study reports that the structures of the intermediates, leading to a blue pigment produced from genipin and methylamine, the simplest primary amine. The mechanism was suggested that the genipin-methylamine monomer is formed through a nucleophilic attack by methylamine on the olefinic carbon at C-3 of genipin, followed by opening of the dihydropyran ring and attack by the secondary amino group on the resulting aldehyde group (FIG. 4A). The blue-pigment was thought formed through oxygen radical-induced polymerization and dehydrogenation of several intermediary pigments.

As disclosed by Sung H W (J Thorac Cardiovasc Surg 2001;122:1208–1218), the simplest component in the blue pigment was a 1:1 adduct. It was suggested that genipin reacts spontaneously with an amino acid to form a nitrogen iridoid, which undergoes dehydration to form an aromatic monomer. Dimerization occurs at the second stage, perhaps by means of radical reaction. The results suggest that genipin may form intramolecular and intermolecular crosslinks with cyclic structure within collagen fibers in biologic tissue (FIG. 4B) or solidifiable collagen-containing biological material.

It is disclosed herein that genipin is capable of reacting with a drug having an amine or amino group. By combining collagen (or a biological material or matrix), genipin and the drug having an amine or amino group, the crosslinked compound may have collagen linked to the drug via genipin as a bridge crosslinker (FIG. 5).

As disclosed and outlined in the application Ser. No. 10/067,130 filed Feb. 4, 2002, entitled "Acellular biological material chemically treated with genipin" by one of the present inventors, the degrees in inflammatory reaction in the animal studies for the. genipin-fixed cellular and acellular tissue were significantly less than their glutaraldehyde-fixed counterparts. Additionally, it was noted that the inflammatory reactions for the glutaraldehyde-fixed cellular and acellular tissue lasted significantly longer than their genipin-fixed counterparts. These findings indicate that the biocompatibility of the genipin-fixed cellular and acellular tissue is superior to the glutaraldehyde-fixed cellular and acellular tissue. It is hypothesized that the lower inflammatory reactions observed for the genipin-fixed cellular and acellular tissue may be due to the lower cytotoxicity of their remaining residues, as compared to the glutaraldehyde-fixed counterparts. In a previous study, it was found that genipin is significantly less cytotoxic than glutaraldehyde (J Biomater Sci Polymer Edn 1999;10:63–78). The cytotoxicity observed for the glutaraldehyde-fixed cellular and acellular tissue seems to result from a slow leaching out of unreacted glutaraldehyde as well as the reversibility of glutaraldehyde-crosslinking. It was observed that when concentrations above 0.05% glutaraldehyde were used to crosslink materials, a persistent foreign-body reaction occurred (J Biomater Sci Polymer Edn 1999;10:63–78).

EXAMPLE #1

Dissolve chitosan powder in acetic acid at about pH 4. Chitosan (MW: about 70,000) was purchased from Fluka Chemical Co. of Switzerland. The deacetylation degree of the chitosan used was approximately 85%. Subsequently, adjust the chitosan solution to approximately pH 5.5 (right before it becomes gelled) with NaOH. Add in drug(s) of interest into the chitosan solution. While loading the drug-containing chitosan onto a stent, adjust the environment to pH 7 with NaOH to solidify the chitosan onto the stent. The process can be accomplished via a continuous assembly line step by providing gradually increasing pH zones as the device passes by. It is further treated with a crosslinking agent, for example genipin to enhance the biodurability and biocompatibility. Note that the chemical formula for chitosan can be found in Mi F L, Tan Y C, Liang H F, and Sung H W, "In vivo biocompatibility and degradability of a novel injectable-chitosan based implant." Biomaterials 2002;23:181–191.

EXAMPLE #2

Add drug(s) of interest into a collagen solution at 4° C. While loading the drug-containing collagen onto a stent, adjust the environment temperature to about 37° C. to solidify the collagen onto the stent. The process can be accomplished via a continuous assembly line step by providing gradually increasing temperature zones as the device passes by. The loading step can be repeated a few times to increase the thickness or total quantity of the drug-containing collagen. The loading step can be started with a high-does drug-containing collagen and then loaded with a lower dose drug-containing collagen or vice versa. It is further treated with a crosslinking agent, for example genipin to enhance the biodurability and biocompatibility. The fixation details could be found elsewhere by Sung et al. (Sung H W, Chang Y, Liang I L, Chang W H and Chen Y C. "Fixation of biological tissues with a naturally occurring crosslinking agent. fixation rate and effects pf pH, temperature, and initial fixative concentration." J Biomed Mater Res 2000;52:77–87).

EXAMPLE #3

Add drug and stent in a NOCC solution at room temperature. The NOCC (named after "Nitrogen Oxygen Carboxylmethyl chitosan") is a chitosan derived compound that is pH sensitive and can be used in drug delivery. This NOCC is water soluble at pH 7. Crosslink the NOCC and drug onto the stent by a crosslinking agent, for example genipin. This is a step of solidification. In one aspect of the present invention, after crosslinking, the drug containing NOCC can be made harder or more solid-like, if needed, by low pH at about 4. The finished stent slowly releases drug when in the body at a pH around neutral.

EXAMPLE #4

Taxol (paclitaxel) is practically water insoluble as some other drugs of interest in this disclosure. Therefore, first mechanically disperse paclitaxel in a collagen solution at about 4° C. Load the drug containing collagen onto a stent and subsequently raise the temperature to about 37° C. to solidify collagen fibers on the stent. The loading step may repeat a plurality of times. Subsequently, crosslink the coated stent with aqueous genipin. The crosslinking on the drug carrier, collagen or chitosan, substantially modify the drug diffusion or eluting rate dependin on the degree of crosslinking.

The "biological substance" made of drug-containing biological material of the present invention and/or the collagen-drug-genipin compound on a stent can be sterilized before use by lyophilization, ethylene oxide sterilization, or sterilized in a series of ethanol solutions, with a gradual increase in concentration from 20% to 75% over a period of several hours. Finally, the drug-loaded stents are rinsed in sterilized saline solution and packaged. The drug carrier, collagen and chitosan, may be fully or partially crosslinked. In one aspect of the present invention, a partially crosslinked collagen/chitosan is biodegradable or bioerodible for drug slow-release.

Figure 6:
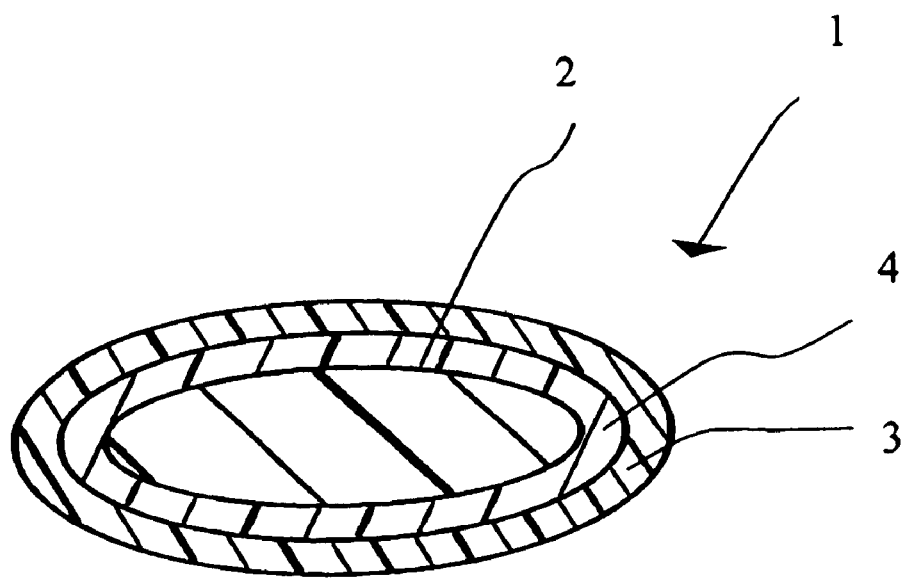
FIG. 6 is an illustrated example of a cross-sectional view for a vascular stent coated with drug-containing collagen crosslinked with genipin according to the principles of the present invention.

FIG. 6 shows an illustrated example of a cross-sectional view for a medical device of a vascular stent 1 coated with drug-containing collagen 3 crosslinked with genipin according to the principles of the present invention. The stent is generally a mesh type tubular prosthesis made of stainless steel, Nitinol, gold, other metals or plastic material. The vascular stent 1 or a stent strut 2 for non-vascular application may further comprise another layer 4 which is slightly different in composition from the drug-containing collagen layer 3. In some aspect, the layer 4 may have higher drug loading and higher adhesive properties enabling the layer to be securely coated onto the stent strut 2 or the medical device. Due to the barrier properties of the crosslinked collagen, drug could only slowly diffuse out of the crosslinked matrix.

Special features for the drug-containing collagen adhesive layer 4 may be characterized by: the layer 4 is securely adhered onto the stent strut; drug is tightly loaded for drug slow release in weeks or months; and collagen is partially crosslinked or fully crosslinked by genipin for stability.

Special features for the drug-containing collagen layer 3 may be characterized by: the layer 3 is securely adhered to layer 4 and vice versa; and drug may be less tightly loaded or collagen may be crosslinked at a lower degree of crosslinkage for drug slow release in days or weeks.

Special features for the drug-loaded collagen and/or drug-loaded chitosan crosslinked by genipin may be characterized by: the crosslinked collagen/chitosan with interpenetrated drug enables drug diffusion at a controlled rate; collagen is tissue-friendly and flexible in deployment; and a crosslinked collagen/chitosan material enhances biocompatibility and controlled biodegradability. The whole process for manufacturing a collagen-drug-genipin or chitosan-drug-genipin compound can be automated in an environmentally controlled facility. Sufficient amount of collagen or drug could be loaded to the exterior side of the stent strut for restenosis mitigation or other therapeutic effects.

From the foregoing description, it should now be appreciated that a novel and unobvious process for making a biological substance comprising an illustrative collagen-drug-genipin compound or chitosan-drug-genipin compound for drug slow release has been disclosed for tissue treatment applications. The process comprises, in combination, mixing a drug with a solidifiable biological material, chemically treating the biological material and/or the drug with a crosslinking agent, loading the solidifiable drug-containing biological material onto a medical device, and solidifying the drug-containing biological material. The resulting biological substance is generally characterized with reduced antigenicity, reduced immunogenicity, and reduced enzymatic degradation and capable of drug slow-release. While the invention has been described with reference to a specific embodiment, the description is illustrative of the invention and is not to be construed as limiting the invention. Various modifications and applications may occur to those who are skilled in the art, without departing from the true spirit and scope of the invention.

What is claimed is:

1. A method for treating a target tissue of a patient comprising, in combination, loading a solidifiable drug-containing biological material onto a medical device, solidifying the drug-containing biological material, crosslinking the biological material with a crosslinking agent, and delivering said medical device to the target tissue and releasing the drug for treating the target tissue.

2. The method of claim 1, wherein the target tissue comprises vulnerable plaque or atherosclerotic plaque, wherein the vulnerable plague is the atherosclerotic plague that is vulnerably prone to rupture.

3. The method of claim 1, wherein the target tissue comprises tumor or cancer.

4. The method of claim 1, wherein the target tissue comprises brain tissue.

5. The method of claim 1, wherein the target tissue comprises vascular vessel.

6. The method of claim 1, wherein the target tissue comprises orthopedic tissue.

7. A method for treating vascular restenosis comprising, in combination, loading a solidifiable drug-containing biological material onto a medical device, solidifying the drug-containing biological material, crosslinking the biological material with a crosslinking agent, and delivering said medical device to a vascular restenosis site for treating the vascular restenosis.

8. The method of claim 1 or 7, wherein the crosslinking agent is genipin.

9. The method of claim 1 or 7, wherein the crosslinking agent is selected from a group consisting of formaldehyde, glutaraldehyde, dialdehyde starch, glyceraldehydes, cyanamide, diimides, diisocyanates, dimethyl adipimidate, carbodiimide, epoxy compound, and mixture thereof.

10. The method of claim 1 or 7, wherein the medical device is a stent.

11. The method of claim 1 or 7, wherein the medical device is a non-stent implant.

12. The method of claim 1 or 7, wherein the medical device is a percutaneous apparatus selected from a group consisting of a catheter, a wire, a cannula, and an endoscopic instrument.

13. The method of claim 1 or 7, wherein the biological material is selected from a group consisting of collagen, gelatin, elastin, chitosan, N, O, carboxylmethyl chitosan, and mixture thereof.

14. The method of claim 1 or 7, wherein the biological material is solidifiable from a phase selected from a group consisting of solution, paste, gel, suspension colloid, and plasma.

15. The method of claim 1 or 7, wherein the drug is selected from a group consisting of analgesics/antipyretics, antiasthamatics, antibiotics, antidepressants, antidiabetics, antifungal agents, antihypertensive agents, anti-inflammatories, antineoplastics, antianxiety agents, immunosuppressive agents, antimigraine agents, sedatives/hypnotics, antipsychotic agents, antimanic agents, antiarrhythmics, antiarthritic agents, antigout agents, anticoagulants, thrombolytic agents, antifibrinolytic agents, antiplatelet agents and antibacterial agents, antiviral agents, antimicrobials, and anti-infectives.

16. The method of claim 1 or 7, wherein the drug is selected from a group consisting of lovastatin, thromboxane $A_2$ synthetase inhibitors, eicosapentanoic acid, ciprostene, trapidil, angiotensin convening enzyme inhibitors, and heparin.

17. The method of claim 1 or 7, wherein the drug is selected from a group consisting of allicin, ginseng extract, flavone, ginkgo biloba extract, glycyrrhetinic acid, and proanthocyanides.

18. A method for treating a target tissue of a patient comprising, in combination, mixing a drug with a solidifiable biological material, crosslinking the biological material with a crosslinking agent, loading the solidifiable drug-containing biological material onto a medical device, solidifying the drug-containing biological material, and delivering said medical device to the target tissue and releasing the drug for treating the target tissue.

19. The method of claim 18, wherein the method comprises chemically linking the drug with the biological material through a crosslinker, wherein the drug comprises at least a crosslinkable functional group.

20. The method of claim 19, wherein the crosslinker is selected from a group consisting of genipin, formaldehyde, glutaraldehyde, dialdehyde stach, glyceraldehydes, cyanamide, diimides, diisocyanates, dimethyl adipirnidate, carbodiimide, epoxy compound, and mixture thereof.

21. The method of claim 18, wherein the crosslinking agent is genipin.

22. The method of claim 18, wherein the crosslinking agent is selected from a group consisting of formaldehyde, glutaraldehyde, dialdehyde starch, glyceraldehydes, cyanarnide, diimides, diisocyanates, dimethyl adipimidate, carbodiimide, epoxy compound, and mixture thereof.

23. The method of claim 18, wherein the medical device is a stent.

24. The method of claim 18, wherein the medical device is a non-stent implant.

25. The method of claim 18, wherein the medical device is a percutaneous apparatus selected from a group consisting of a catheter, a wire, a cannula, and an endoscopic instrument.

26. The method of claim 18, wherein the biological material is selected from a group consisting of collagen, gelatin, elastin, chitosan, N, O, carboxylmethyl chitosan, and mixture thereof.

27. The method of claim 18, wherein the biological material is solidifiable from a phase selected from a group consisting of solution, paste, gel, suspension, colloid, and plasma.

28. The method of claim 18, wherein the drug is selected from a group consisting of analgesics/antipyretics, antiasthamatics, antibiotics, antidepressants, antidiabetics, antifungal agents, antihypertensive agents, anti-inflammatories, antineoplastics, antianxiety agents, immunosuppressive agents, antimigraine agents, sedatives/hypnotics, antipsychotic agents, antimanic agents, antiarrhythmics, antiarthritic agents, antigout agents, anticoagulants, thrombolytic agents, antifibrinolytic agents, antiplatelet agents and antibacterial agents, antiviral agents, antimicrobials, and anti-infectives.

29. The method of claim 18, wherein the drug is selected from a group consisting of lovastatin, thromboxane $A_2$ synthetase inhibitors, eicosapentanoic acid, ciprostene, trapidil, angiotensin convening enzyme inhibitors, and heparin.

30. The method of claim 18, wherein the drug is selected from a group consisting of allicin, ginseng extract, flavone, ginkgo biloba extract, glycyrrhetinic acid, and proanthocyanides.

* * * * *